United States Patent [19]

Lundquist

[11] Patent Number: 4,667,575
[45] Date of Patent: May 26, 1987

[54] PUMP ACTUATOR ASSEMBLY

[75] Inventor: Ingemar H. Lundquist, Oakland, Calif.

[73] Assignee: Valleylab, Inc., Boulder, Colo.

[21] Appl. No.: 156,612

[22] Filed: Jun. 5, 1980

Related U.S. Application Data

[63] Continuation of Ser. No. 818,005, Jul. 22, 1977, abandoned.

[51] Int. Cl.$^4$ .............................................. F01B 19/00
[52] U.S. Cl. ..................................... 92/98 R; 417/383
[58] Field of Search ..................... 417/383, 389, 395; 92/13.2, 98 R, 98 D, 158, 160; 60/583, 562

[56] References Cited

U.S. PATENT DOCUMENTS

| | | | |
|---|---|---|---|
| 1,622,896 | 3/1927 | Lowenstein | 60/583 |
| 1,764,712 | 6/1930 | Brackett et al. | 417/439 X |
| 1,769,044 | 7/1930 | Stevens | 417/383 X |
| 2,667,184 | 1/1954 | Hailer et al. | 92/103 R |
| 2,710,119 | 6/1955 | Steele | 417/511 X |
| 2,902,944 | 9/1959 | Etten | 417/568 |
| 2,915,016 | 12/1959 | Weaver et al. | 417/388 |
| 2,963,976 | 12/1960 | Schaurte | 417/383 |
| 3,099,260 | 7/1963 | Birtwell | 417/389 X |
| 3,183,672 | 5/1965 | Morgan | 60/583 |
| 3,212,447 | 10/1965 | Browne | 92/48 X |
| 3,680,789 | 8/1972 | Wagner | 417/395 |
| 3,976,402 | 8/1976 | Lundquist | 92/98 D |
| 4,047,850 | 9/1977 | Berthelot | 417/383 |

FOREIGN PATENT DOCUMENTS 2556465  6/1977  Fed. Rep. of Germany ........ 92/158

Primary Examiner—Edward K. Look
Attorney, Agent, or Firm—Flehr, Hohbach, Test, Albritton & Herbert

[57] ABSTRACT

Pump actuator assembly for use in operating a pump for supplying intravenous liquid to a patient which comprises a housing having a sealed chamber therein with a portion thereof being covered by a flexible membrane. A plunger is mounted in the housing so that a portion thereof is disposed in the sealed chamber for movement between innermost and outermost positions. A constant quantity of liquid fills the sealed chamber. A booth encloses the portion of the plunger disposed in the fluid. A liquid-tight seal is provided between the booth and the housing to permit the plunger to be moved between the innermost and outermost positions so that the flexible membrane can be caused to move between extended and retracted positions.

2 Claims, 2 Drawing Figures

U.S. Patent     May 26, 1987     4,667,575
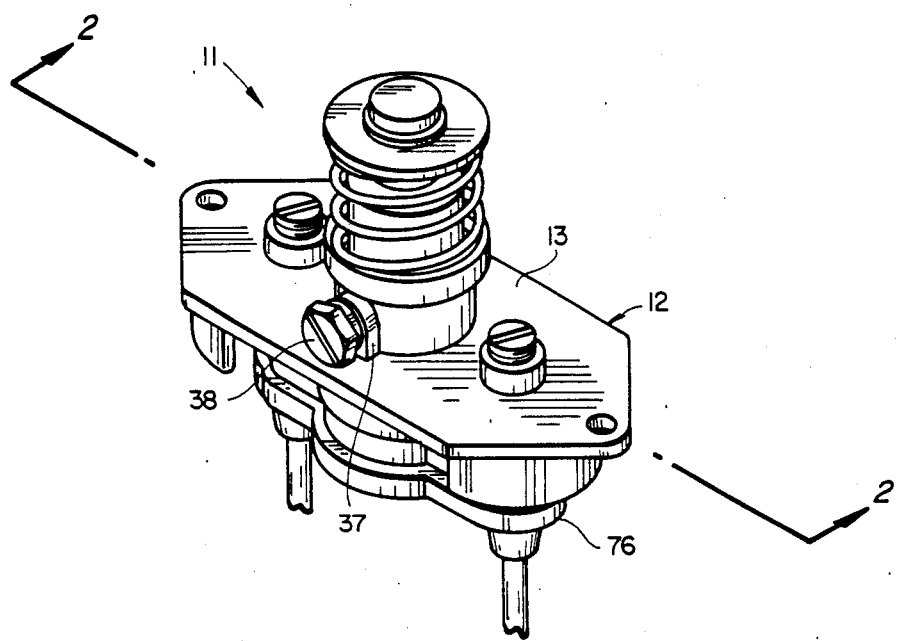
FIG_1
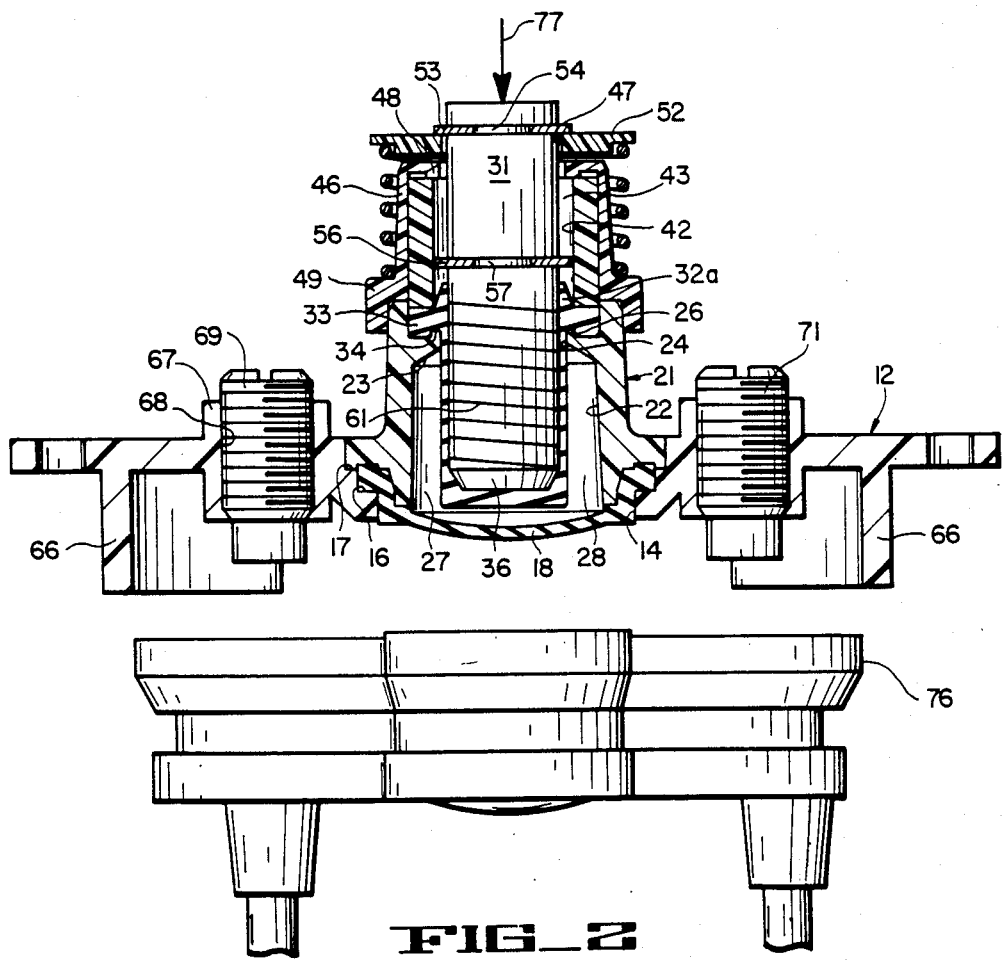
FIG_2

PUMP ACTUATOR ASSEMBLY

This is a continuation of application Ser. No. 818,005 filed July 22, 1977 now abandoned.

BACKGROUND OF THE INVENTION

In copending application, Ser. No. 689,115, filed on May 24, 1976, there is disclosed an intravenous pumping system which includes a pump actuator assembly 46 in which a plunger moves into and out of a chamber having a portion thereof covered by a flexible member which is filled with a constant quantity of liquid. It has been found to be very difficult to control leaks between the plunger and the housing. Such leaks permit air to enter into the chamber and thereby degrade the accuracy of the pumping operation which is to be carried out by the pump actuator assembly. There is therefore, need for an improved pump actuator assembly which will overcome this disadvantage.

SUMMARY OF THE INVENTION AND OBJECTS

The pump actuator assembly is for use in operating a pump for supplying an intravenous liquid to a patient. It is comprised of a housing having a sealed chamber therein with a portion thereof being covered by a flexible membrane. A plunger is mounted in the housing so that a portion thereof is disposed in the sealed chamber for movement between innermost and outermost positions in the sealed chamber. A constant quantity of liquid fills the sealed chamber. A booth encloses the portion of the plunger which is disposed within the liquid. Means is provided for forming a liquid-tight seal between the booth and the housing so that as the plunger is moved between the innermost and outermost positions, the flexible membrane is caused to be moved between extended and retracted positions.

In general, it is an object of the present invention to provide a pump actuator assembly which has greatly improved accuracy.

Another object of the invention is to provide a pump actuator assembly of the above character in which it is possible to provide for a return stroke for the plunger without danger of causing the entrance of air or degassing the liquid.

Another object of the invention is to provide a pump actuator assembly of the above character in which an excellent seal is obtained between the plunger and the housing.

Another object of the invention is to provide a pump actuator assembly of the above character which is reliable and also trouble-free.

Additional objects and features of the invention will appear from the following description in which the preferred embodiment is set forth in detail in conjunction with the accompanying drawings.

BRIEF DESCRIPTION OF THE DRAWINGS

FIG. 1 is an isometric view of a pump actuator assembly incorporating the present invention with the pump mounted therein.

FIG. 2 is a cross-sectional view taken along line 2—2 of FIG. 1 showing the pump separated by a small distance from the pump actuator assembly.

DESCRIPTION OF THE PREFERRED EMBODIMENT

The pump actuator assembly 11 which is shown in FIGS. 1 and 2 of the drawings is similar to the pump actuator assembly disclosed in copending application, Ser. No. 689,115, filed on May 24, 1976. As disclosed therein, it consists of a pump receptacle 12 formed of a suitable material such as plastic. The pump receptacle is provided with a flat, plate-like member 13. The plate-like member 13 has a centrally disposed opening 14 formed therein. First and second annular steps 16 and 17 are formed in the pump receptacle 12 and are concentric with the opening 14. A flexible membrane 18 having a circular configuration is disposed within the opening 14 and has an outer step annular margin 19 which seats upon the step 16 and is clamped therein by reservoir forming member 21. The reservoir forming member 21 is formed of a suitable material such as plastic and is bonded to the plastic pump receptacle 12 by suitable means such as ultrasonic bonding so that a liquid-tight seal is formed between the reservoir forming member 21 and the pump receptacle 12 and the flexible member 18.

The reservoir forming member 21 is provided with the central cylindrical bore 22. The reservoir forming member 21 is also provided with an inwardly extending flange 23 that overlies the central bore 22 and which is provided with a centrally disposed opening or hole 24. The flange 23 is provided with an upstanding annular lip 26 immediately adjacent to opening 24. The central bore 22 forms a chamber 27 which is filled with a constant quantity of a relatively incompressible liquid 28 of a suitable type such as Dow Corning silicone fluid No. 700.

A plunger or piston 31 extends through the opening 24 provided in the flange 23 and has a portion thereof disposed within the chamber 27. Means is provided for establishing a liquid-tight seal between the plunger 31 and the annular flange 23 of the reservoir forming member 21 and consists of a booth or boot 32 formed of a suitable material such as a natural medical grade rubber or a synthetic rubber such as neoprene which encloses a portion of the plunger 31 within the chamber 27 and which is provided with an outwardly extending annular flange 33 that seats over the top of the flange 23 of the reservoir forming member 21. The lower surface of the flange 33 is cemented to the upper surface of the flange 23 so as to provide an absolutely liquid-tight seal between the two flanges. The flange 33 is provided with an annular recess 34 which accommodates the annular lip 26 on the flange 23. The lower extremity of the plunger 31 is provided with a chamber 36. As can be seen, particularly from FIG. 2, the booth 32 fits snugly over the lower extremity of the plunger 31 and serves to ensure that no air, gas or other substance can pass between the piston or plunger 31 and the annular flange 23 so that when chamber 27 is filled with liquid through the filling port 37 which is then closed by the filling screw 38, a constant quantity of liquid will be retained within the chamber 27.

Means is provided for clamping the flange 33 of the booth 32 into firm seating engagement with the flange 23 of the reservoir forming member 21 and consists of a sleeve 41 formed of a suitable material such as plastic which has its lower extremity seated over the flange 33. The sleeve 41 is provided with a central bore 42 which is substantially greater than the diameter of the plunger 31 so that there is provided an annular space 43 between the plunger 31 and the sleeve 41. The plunger 31 extends upwardly through the bore 42. A cap 46 is provided which is formed of a suitable material such as plastic. The cap 46 has a centrally disposed hole 47 which accommodates the plunger 31. It is also provided with a downwardly extending lip 48 that is adapted to engage the upper extremity of the sleeve 41. The cap 46 is also provided with a downwardly and outwardly extending flange 49 which seats over the top of the upper extremity of the reservoir forming member 21 and is secured thereto in a suitable manner such as by cement to firmly hold the cap in place and at the same time to engage the sleeve 41 to hold it in tight fitting engagement with the flange 33 of the booth 32 so that a good liquid-tight seal is formed with the flange 23 of the reservoir forming member 21. Means is provided for yieldably urging the plunger for movement from an innermost position to an outermost position and consists of a helical spring 51 which is seated on the outside of the cap 46 and has its lowermost extremity engaging the flange 49 of the cap. The upper extremity of the spring 51 engages a washer 52 formed of a suitable material such as plastic which is slidably mounted on the upper extremity of the piston 31. The washer 52 is retained on the upper extremity of the plunger 31 by an E ring 53 which is seated in an annular groove 54 provided in the plunger 31. Thus it can be seen that spring 51 continuously applies a yieldable force to the plunger to move it towards it outermost position. The outermost position of the plunger is determined by another E ring 56 disposed within the bore 42 of the sleeve 41 and which is seated in an annular recess 57 provided in the plunger 31 intermediate the ends of the same. The E ring 56 is adapted to engage the upper extremity of the cap 46 and thus limits the outermost travel of the plunger 31. The innermost position of travel is determined by the E ring 53 striking the cap 52.

Although the Teflon which is utilized for the plunger piston 31 is relatively slippery, so as to permit relative movement between the booth 32 and the plunger 31 during movement of the plunger between innermost and outermost positions, it has been found that it is desirable to provide lubrication of a suitable type to facilitate this movement and to inhibit any binding between the booth 32 and the plunger 31. One lubricant found particularly satisfactory is a silicon lubricant identified as Dow-Corning 1265. In order to enhance the lubricating quality of this lubricant it has been found that it is also desirable to mix the lubricant with a small amount of fine mica powder.

In order to ensure that the lubricant which is provided on the piston to facilitate stretching action of the booth 32 during movement of the plunger 31 between its innermost and outermost positions, it is desirable to provide a plurality of very fine helical grooves or recesses 61 much like threads on the lower extremity of the piston or plunger 31 within the confines of the booth 32. For example, as many as 30-50 threads per inch may be provided. The grooves or recesses 31 are relatively shallow and are formed in this manner to that the booth 32 will have no tendency to be deformed into the grooves 61 so that the booth will provide a substantially constant volume during movement of the piston or plunge 31 between its innermost and outermost positions. The grooves preferably should extend from the lowermost extremity of the plunger or piston 31 up to a point near the upper extremity of the booth 32. The upper extremity of the booth 32 is provided with an inwardly extending lip 32a which tightly engages the plunger 31 and serves to prevent air from entering between the booth 32 and the plunger 31. They should not extend beyond the upper extremity of the booth to avoid any tendency for air to leak between the plunger 31 and the upper end of the booth. Any air which is trapped between the booth 32 and the plunger 31 would be compressible and thus make possible undesirable variations in the volume of fluid which is discharged by the pump that is being driven by the pump actuator assembly 11. The fine grooves 31 serve to retain the silicone lubricant from the piston or plunger 31 which is engaged by the booth 32.

The remaining portions of the pump actuator assembly 11 are substantially identical to that described in copending application, Ser. No. 689,115, filed on May 24, 1976. Thus there is provided a pair of downwardly extending semi-circular extensions 66 on opposite ends of the plate-like member 13. It is also provided with a pair of bosses 67 which have internally threaded bores 68. Valve engagement screws 69 and 71 are threaded into the bores 68.

A pump assembly 76 of the type described in copending application, Ser. No. 689,115, filed on May 24, 1976, is adapted to be seated within the pump actuator assembly 11 in the manner described in that copending application. As also explained in that copending application, the plunger 31 is moved downwardly as indicated by the arrow 37 by an actuator arm 26 controlled by a controller of the type described in copending application, Ser. No. 689,115, filed on May 24, 1976. When the plunger 31 is moved downwardly into the chamber 27 the booth 32 is stretched to cause the flexible membrane 18 to be bulged outwardly as shown in Fig. 2 and to cause a similar movement in the membrane (not shown) of the pump 76 to cause the pumping of liquid by the pump in the manner described in copending application, Ser. No. 689,115, filed on May 24, 1976. As soon as the actuator arm moves upwardly, the plunger 31 will move upwardly under the force of the spring 51 to permit the flexible membrane 18 to return to its normal position. Thus it can be seen that the membrane carried by the pump 76 will follow the membrane 18 so that a liquid will be pumped by the pump 76. As can be seen, the pump 76 is readily removable from the pump receptacle 12 and can be readily disposed of.

From the construction hereinbefore described, it can be seen that the pump actuator assembly can be permanently assembled to ensure that the chamber 27 will always be liquid-tight and that a constant quantity of liquid will be retained in the chamber 27. This ensures that the same displacement of the membrane 18 will occur for each identical movement of the plunger 31. The use of the lubricant ensures that the operation of the pump actuator assembly 11 will be trouble-free. The purpose of the grooves 61 is to ensure that the entire surface of the plunger 31 which is in engagement with the booth 32 is continuously wetted or lubricated. In order to ensure additional wetting of the surface of the plunger 31 with the lubricant, it may be desirable to lightly sand blast the surface of the same. This sand blasting is provided in a region above the groove 61 up to the E ring 56. This ensures that this surface will continuously be wetted by the lubricant and help to serve to form an airtight seal between the lip 32a and the plunger 31.

It is apparent from the foregoing that there has been provided a new and improved pump actuator which is particularly advantageous in that it is leakproof and trouble-free.

What is claimed is:

1. In a pump actuator assembly for use in operating a the outer extremity of the flange of the booth to the flange carried by the reservoir forming member for forming a liquid-tight seal between the reservoir and the booth, said means for clamping the flange of the booth to the flange of the reservoir forming member including a sleeve through which the plunger extends and a cap engaging the sleeve and secured to the reservoir forming member, a constant quantity of liquid filling said reservoir, the plunger being movable between innermost and outermost positions in the reservoir to cause movement of the flexible membrane, means for yieldably urging said plunger towards its outermost position and cooperative means carried by the plunger and the reservoir forming member for limiting the movement of the plunger between innermost and outermost positions.

2. In a pump actuator assembly for use in operating a pump for supplying intravenous liquid to a patient, a rigid housing having an opening therein, a flexible mempump for supplying intravenous liquid to a patient, a pump receptable having an opening therein, a flexible membrane disposed in said opening, means for establishing a liquid-tight seal between the membrane and the pump receptacle, means forming a liquid-tight reservoir overlying said membrane in which said membrane forms a portion of the liquid-tight reservoir, said means forming a reservoir being provided by a reservoir forming member having a flange with a central opening, a plunger mounted in said opening and extending therethrough, a stretchable booth enclosing the portion of said plunger in said reservoir and having a flange, means carried by the reservoir forming member for clamping brame closing said opening to form a sealed chamber in said housing, a plunger slidably mounted in said housing so that a portion thereof is disposed in the sealed chamber for movement between innermost and outermost positions, a constant quantity of liquid filling said sealed chamber, a booth formed of rubber-like material enclosing and snugly fitting the portion of the plunger disposed in the liquid, the portion of the plunger in engagement with the booth being provided with a plurality of grooves, a lubricant disposed in the grooves and between the plunger and the booth, and means forming a liquid tight seal between the booth and the housing so that as the plunger is moved between said innermost and outermost positions, said flexible membrane is caused to move between extended and retracted positions, said membrane providing an exterior surface which is readily accessible.

* * * * *